United States Patent [19]

Bauer et al.

[11] Patent Number: 4,645,526
[45] Date of Patent: Feb. 24, 1987

[54] HERBICIDAL AGENTS

[75] Inventors: Klaus Bauer, Rodgau; Hermann Bieringer, Eppstein/Taunus; Hans Schumacher, Flörsheim am Main, all of Fed. Rep. of Germany

[73] Assignee: Hoechst Aktiengesellschaft, Frankfurt am Main, Fed. Rep. of Germany

[21] Appl. No.: 711,402

[22] Filed: Mar. 13, 1985

[30] Foreign Application Priority Data

Mar. 15, 1984 [DE] Fed. Rep. of Germany ....... 3409432

[51] Int. Cl.⁴ ..................... A01N 43/28; A01N 47/30
[52] U.S. Cl. ............................................ 71/88; 71/120
[58] Field of Search ................................. 71/88, 120

[56] References Cited

PUBLICATIONS

SIPCAM, "Herbicidal Composition for Grains," (1979) CA 91: 118676g (1979).
Hoechst, "Herbicidal Composition," (1979) CA 92: 175774g (1980).
Bieringer et al I, "Tolerance of Graminaceous, etc.," (1982) CA 98: 48574r (1983).
Quadranti et al, "Synergistic Agents and, etc.," (1982) CA 96: 157409v (1982).
Schwer et al, "Herbicidal Combinations," (1978) CA 89: 124577a (1978).
Bieringer et al II, "Herbicidal Composition," (1980) CA 93: 2263g (1980).
Levitt, "Herbicidal Sulfonamide, etc.," (1980) CA 93: 63626z (1980).
Hawkins et al, "Counteracting Herbicides, etc.," (1980) CA 95: 19713t (1981).
Anon, "Herbicidal Mixtures," (1981) CA 94: 134014g (1981).
Colby, "Calculating Synergistic, etc.," Weeds, 15, pp. 20-22 (1967).

Primary Examiner—Glennon H. Hollrah
Assistant Examiner—Robert Lelkes
Attorney, Agent, or Firm—Curtis, Morris & Safford

[57] ABSTRACT

Herbicidal agents containing an active substance of the formula (I)

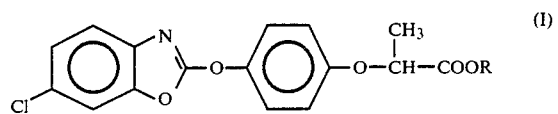

in which R denotes alkyl, in combination with an active substance of the formula (II)

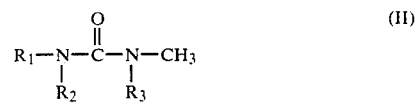

in which $R_1$ denotes phenyl, which is substituted by chlorine or $(C_1-C_3)$-alkyl, or denotes benzothiazolyl, $R_2$ denotes H or methyl and $R_3$ denotes H, methyl or methoxy, show super-additive actions and are outstandingly suitable for combating harmful plants in cereals.

4 Claims, No Drawings

HERBICIDAL AGENTS

Herbicides of the 6-chloro-benzoxazolyloxyphenoxy-propionic acid type, such as are known from German Patent Application No. A 2,640,730 (U.S. Pat. No. 4,130,413), have a good herbicidal activity against various economically important harmful grasses when applied by the post-emergence method. However, they frequently cannot be employed selectively in useful cereal crops because lasting damage may occur in the form of inhibition of growth or shortening of stalks.

Surprisingly, it has now been found that the tolerance of the herbicides can be considerably improved if they are used together with known cereal herbicides on a urea basis. Unexpected super-additive increases in action have furthermore been observed with these combinations according to the invention.

The present invention thus relates to herbicidal agents which contain an active substance of the formula (I)

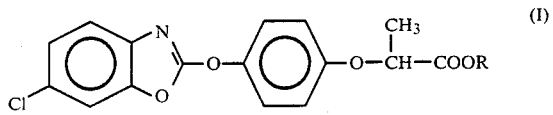

in which R denotes $(C_1-C_4)$-alkyl,
in combination with an active substance of the formula (II)

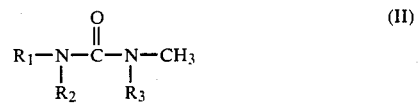

in which
$R_1$ denotes phenyl, which is substituted by one or two radicals from the group comprising chlorine and $(C_1-C_3)$-alkyl, or denotes benzothiazolyl,
$R_2$ denotes H or methyl and
$R_3$ denotes H, methyl or methoxy.

A particularly suitable compound of the formula (I) is that in which R denotes $C_2H_5$ [compound (Ia)=ethyl 2-(4-(6-chloro-benzoxazolyl-2-oxy)-phenoxy)-propionate].

Examples of the compounds of the formula (II) which may be mentioned are chlorotoluron (3-(3-chloro-4-methylphenyl)-1,1-dimethylurea), diuron (3-(3,4-dichlorophenyl)-1,1-dimethylurea), isoproturon (3-(4-isopropylphenyl)-1,1-dimethylurea), methabenzthiazuron (3-(benzothiazol-2-yl)-1,3-dimethylurea), monolinuron (3-(4-chlorophenyl)-1-methoxy-1-methylurea), linuron (3-(3,4-dichlorophenyl)-1-methoxy-1-methylurea) and 3-(3-chloro-4-isopropylphenyl)-1-methoxy-1-methyl-urea. Of these, particularly preferred active substances which may be mentioned are chlorotoluron, isoproturon and methabenzthiazuron, and the particularly preferred active substance is isoproturon.

The herbicidal agents according to the invention can advantageously be used for selectively combating gramineous and broad-leaved weeds in cereals, in particular in rye and wheat, preferably wheat. Harmful effects of compounds of the formula (I) on the crop plants are eliminated by the influence of the compounds of the formula (II). The compounds of the formula (II) accordingly have a surprising safener or antidote action for the compounds of the formula (I).

Surprising synergistic increases in action have also been found in the combinations according to the invention, i.e. the herbicidal actions observed with the mixtures of (I) and (II) were more intense than was to be expected on the basis of the activities of the individual components.

The two active substances of the formulae (I) and (II) are advantageously applied together; however, they can also be applied separately. The combinations according to the invention are as a rule applied by the postemergence method.

The present invention thus also relates to a method for combating harmful plants in cereals, which comprises applying an effective amount of a compound of the formula (I) in combination with a compound of the formula (II), together or successively, to the crop plants or the areas under cultivation. The present invention also relates to a method of protecting crop plants from the phytotoxic effects of herbicides of the formula (I), which comprises applying a compound of the formula (II), together with the herbicide of the formula (I) or successively, to the crop plants or the areas under cultivation.

The gramineous herbicide of the formula (I) is employed in a dosage in the range from 0.05 to 0.3 kg of active substance/ha, while the urea derivatives of the formula (II) are applied in dosages in the range from 0.3 to 3.0 kg of active substance/ha. The ratio of active substances of the formula (I) to active substances of the formula (II) can vary within the range from 1:1 to 1:60 and is preferably in the range from 1:3 to 1:30.

The herbicidal combinations according to the invention can be used either as tank mixes, in which the active substances are only mixed with one another immediately before the application, or as finished formulations. As finished formulations, they can be formulated in the form of wettable powders, emulsifiable concentrates, solutions which can be sprayed, dusting agents or granules, and contain the usual formulation auxiliaries, such as wetting agents, tackifiers, dispersants, solid or liquid inert substances and grinding auxiliaries or solvents.

Wettable powders are products which are uniformly dispersible in water and which, in addition to the active ingredient and as well as a diluent or inert substance, also contain customary wetting agents, such as polyoxyethylated alkylphenols, polyvinyl alcohol, polyoxydethylated oleylamines or stearylamines and alkyl- or alkylphenyl-sulfonates, and customary dispersants, such as sodium lignin-sulfonate, potassium lignin-sulfonate or calcium lignin-sulfonate, sodium 2,2'-dinaphthylmethane-6,6'-disulfonate or sodium oleyl methyl tauride.

Emulsifiable concentrates are obtained by dissolving the active substance in an organic solvent, such as butanol, cyclohexanone, dimethylformamide, xylene or higher-boiling aromatics, and adding a non-ionic wetting agent, for example a polyoxyethylated alkylphenol, a polyoxyethylated oleylamine or stearylamine or an alkyl- or alkylphenyl-sulfonate. Granules can be prepared either by spraying the active substance onto an adsorbent, granular inert material or by applying active substance concentrates to the surface of carriers, such as sand or kaolinites, or a granular inert material by means of adhesives, such as polyvinyl alcohol, sodium polyacrylate or mineral oils.

The concentrations of the active substances in the commercially available formulations can vary. In wettable powders, the total concentration of active substance varies between about 20% and 90%, the remainder consisting of the abovementioned formulation additives. The active substance concentration in emulsifiable concentrates is about 10% to 80%.

For use, the commercially available concentrates are diluted in the customary manner, if appropriate, for example by means of water, in the case of wettable powders and emulsifiable concentrates. The required application amount varies according to the external conditions, such as temperature, humidity and the like. It can vary within wide limits, in particular in the range from 0.35 to 3.5 kg of active substance/ha.

The agents according to the invention can be combined with other herbicides, insecticides and fungicides; in particular, other herbicidal active substances can be added, depending on the particular weed problem.

A. FORMULATION EXAMPLES

Example 1

A wettable powder which is easily dispersible in water is obtained by thoroughly mixing 4.0 parts by weight of ethyl 2-[4-(6-chloro-benzoxazolyl-2-oxy)-phenoxy]-propanoate [compound (Ia)], 40.0 parts by weight of isoproturon, 35.0 parts by weight of synthetic silicic acid, 8.0 parts by weight of calcium lignin-sulfonate, 1.0 part by weight of arylsulfonate (Na salt), 5.0 parts by weight of sodium oleyl methyl tauride, 4.0 parts by weight of polyvinyl alcohol and 3.0 parts by weight of basic aluminum silicate (kaolinite) in a drum mixer and then comminuting the mixture on a pinned disc mill at 3,000 rpm. The ground material obtained is mixed again and finely ground at 12,000 rpm.

Example 2

A wettable powder which is readily dispersible in water is obtained by thoroughly mixing 4.0 parts by weight of compound (Ia), 48.0 parts by weight of methabenzthiazuron, 30.0 parts by weight of synthetic silicic acid, 7.0 parts by weight of potassium lignin-sulfonate, 5.0 parts by weight of arylsulfonate (Na salt), 4.0 parts by weight of sodium oleyl methyl tauride and 2.0 parts by weight of polyvinyl alcohol in a drum mixer and then grinding the mixture, as described under Example 1, initially at 3,000 rpm and then at 12,000 rpm.

Example 3

A wettable powder which is readily dispersible in water is obtained by thoroughly mixing 3.0 parts by weight of compound (Ia), 45.0 parts by weight of methabenzthiazuron, 32.0 parts by weight of synthetic silicic acid, 7.0 parts by weight of potassium lignin-sulfonate, 5.0 parts by weight of arylsulfonate (Na salt), 4.0 parts by weight of sodium oleyl methyl tauride and 4.0 parts by weight of polyvinyl alcohol in a drum mixer and then grinding the mixture, as described under Example 1, initially at 3,000 rpm and then at 12,000 rpm.

Example 4

A powder which is readily dispersible in water is obtained by thoroughly mixing 3.0 parts by weight of compound (Ia), 36.0 parts by weight of chlorotoluron, 25.0 parts by weight of synthetic silicic acid, 15.0 parts by weight of basic aluminum silicate (kaolinite), 12.0 parts by weight of ethoxylated triisodecanol, 6.0 parts by weight of potassium lignin-sulfonate and 3.0 parts by weight of polyvinyl alcohol in a drum mixer and then grinding the mixture, as described under Example 1, initially at 3,000 rpm and then at 12,000 rpm.

Example 5

A powder which is readily dispersible in water is obtained by thoroughly mixing 3.0 parts by weight of compound (Ia), 45.0 parts by weight of chlorotoluron, 30.0 parts by weight of synthetic silicic acid, 10.0 parts by weight of basic aluminum silicate (kaolinite), 4.0 parts by weight of potassium lignin-sulfonate, 4.0 parts by weight of Na oleyl methyl tauride and 4.0 parts by weight of polyvinyl alcohol in a drum mixer and then grinding the mixture, as described under Example 1, initially at 3,000 rpm and then at 12,000 rpm.

Example 6

An emulsifiable concentrate is obtained from 3.0 parts by weight of compound (Ia), 24.0 parts by weight of monolinuron, 40.0 parts by weight of xylene, 15.0 parts by weight of cyclohexanone, 10.0 parts by weight of fatty acid polyglycol ester, 5.5 parts by weight of the Ca salt of an alkylarylsulfonic acid and 2.5 parts by weight of alkylaryl polyglycol ether.

To prepare the emulsifiable concentrate, the two active substances are dissolved in the stated amounts of solvent, with gentle warming, and the emulsifiers are then added, with stirring. The essentially clear solution formed is filtered and then investigated for its emulsion quality.

B. BIOLOGICAL EXAMPLES

The combinations according to the invention were applied to crop plants in the 4-6-leaf stage by the post-emergence method. The plants were grown for four weeks under greenhouse conditions. The herbicidal actions were then determined by visual rating.

The experimental results according to the following table demonstrate that compound (Ia) already causes distinct damage to wheat in the dosages effective against gramineous weeds. When the combinations according to the invention are used, the harmful effect on wheat is eliminated, and in addition the herbicidal activity against the gramineous weeds is synergistically increased. The combinations according to the invention are thus outstandingly suitable for selectively combating gramineous and dicotyledon weeds in cereal crops by the post-emergence method.

The synergism is demonstrated by comparing the additive degree of action calculated from the actions of the individual components with the degree of action found experimentally with the active substance combinations. The additive degree of action is calculated from the equation by S. R. Colby (c.f. Calculating synergistic and antagonistic responses of herbicide combinations, Weeds, 15, 1967, pages 20 to 22).

This formula is as follows:

$$E = X + Y - \frac{X \cdot Y}{100}$$

in which
X denotes % damage by herbicide (I) at an application amount of x kg/ha,
Y denotes % damage by herbicide (II) at an application amount of y kg/ha,
E denotes the expected % damage of herbicides (I)+(II) at an application amount of x+y kg/ha.

If the actual damage is greater than calculated, the action of the active substance combination is more than additive, i.e. a synergistic effect exists. This is demonstrated with the aid of the biological examples in the following table, the right-hand column of the results of the combination treatments giving, in parentheses, the additive actions calculated from the above formula.

TABLE

Herbicidal activity and selectivity by the post-emergence method (action in %)

| Active substance | Dose kg of active substance/ha | TA | AVF | ALM | STM |
|---|---|---|---|---|---|
| (Ia) | 0.2 | 30 | 95 | 100 | 15 |
|  | 0.1 | 10 | 80 | 90 | 5 |
|  | 0.050 | 0 | 60 | 65 | 0 |
|  | 0.025 | 0 | 40 | 10 | 0 |
| Chlortoluron | 0.5 | 0 | 40 | 65 | 85 |
| Isoproturon | 0.40 | 0 | 50 | 60 | 95 |
| Methabenzthiazuron | 0.75 | 0 | 75 | 60 | 100 |
| (Ia) + Chlortoluron | 0.2 + 0.5 | 5 | 100 | 100 | 95 |
|  | 0.1 + 0.5 | 0 | 100(88) | 100 | 90 |
|  | 0.050 + 0.5 | 0 | 97(76) | 95(88) | 95 |
|  | 0.025 + 0.5 | 0 | 90(74) | 85(68.5) | 90 |
| (Ia) + Isoproturon | 0.2 + 0.38 | 0 | 100 | 100 | 98 |
|  | 0.1 + 0.38 | 0 | 100(90) | 99 | 95 |
|  | 0.050 + 0.38 | 0 | 95(80) | 92(84) | 95 |
|  | 0.025 + 0.38 | 0 | 85(70) | 75(69) | 95 |
| (Ia) + Methabenzthiazuron | 0.2 + 0.75 | 2 | 100 | 100 | 100 |
|  | 0.1 + 0.75 | 0 | 100 | 100 | 100 |
|  | 0.050 + 0.75 | 0 | 92 | 97(89) | 100 |
|  | 0.025 + 0.75 | 0 | 80 | 85(64) | 100 |

(Ia) = Ethyl 2-[4-(6-chloro-benzoxazolyl-2-oxy)-phenoxy]-propionate
TA = Wheat
ALM = Alopecurus myosuroides
AVF = Avena fatua
STM = Stellaria media

We claim:

1. A herbicidal agent which consists essentially of a combination of (a) ethyl 2-[4-(6-chlorobenzoxazolyl-2-oxy)-phenoxy]-propionate and (b) 3-(4-isopropyl-phenyl)-1,1-dimethylurea or 3-(3-chloro-4-methyl-phenyl)-1,1-dimethylurea, in a ratio by weight from 1:2 to 1:20.

2. A herbicidal agent as claimed in claim 1, wherein the ratio by weight is from 1:2 to 1:5.

3. A method of protecting cereal plants from the phytotoxic effects of ethyl 2-[4-(6-chlorobenzoxazolyl-2-oxy)-phenoxy]-propionate, which comprises applying 3-(4-isopropyl-phenyl)-1,1-dimethylurea or 3-(3-chloro-4-methylphenyl)-1,1-dimethylurea, together with ethyl 2-[4-(6-chlorobenzoxazolyl-2-oxy)-phenoxy]-propionate or successively, in a ratio by weight of 1:2 to 1:20, to the plants or an area under cultivation with the plants.

4. A herbicidal agent as claimed in claim 3, wherein the ratio by weight is from 1:2 to 1:5.

* * * * *